US008192958B2

(12) United States Patent
Adie et al.

(10) Patent No.: US 8,192,958 B2
(45) Date of Patent: Jun. 5, 2012

(54) NUCLEIC ACID ISOLATION USING POLIDOCANOL AND DERIVATIVES

(75) Inventors: Sigrid Adie, Munich (DE); Hermann Leying, Rotkreuz (CH); Nicole Nachbaur, Murnau-Seehausen (DE); Eberhard Russmann, Huenenberg See (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/314,739

(22) Filed: Dec. 8, 2011

(65) Prior Publication Data

US 2012/0100599 A1 Apr. 26, 2012

Related U.S. Application Data

(62) Division of application No. 12/001,670, filed on Dec. 11, 2007, now abandoned.

(30) Foreign Application Priority Data

Dec. 11, 2006 (EP) .................................... 06025539

(51) Int. Cl.
C12Q 1/70 (2006.01)
C12Q 1/68 (2006.01)
C07C 21/00 (2006.01)
(52) U.S. Cl. .................. 435/72; 435/5; 435/6; 536/25.4
(58) Field of Classification Search .................. None
See application file for complete search history.

(56) References Cited

U.S. PATENT DOCUMENTS

| 4,683,195 | A | 7/1987 | Mullis et al. |
| 5,130,238 | A | 7/1992 | Malek et al. |
| 5,210,015 | A | 5/1993 | Gelfand et al. |
| 5,386,024 | A | 1/1995 | Kacian et al. |
| 5,487,972 | A | 1/1996 | Gelfand et al. |
| 5,804,375 | A | 9/1998 | Gelfand et al. |
| 6,737,235 | B1 | 5/2004 | Cros et al. |
| 2004/0230048 | A1 | 11/2004 | Conrad |
| 2005/0079535 | A1 | 4/2005 | Kirchgesser et al. |

FOREIGN PATENT DOCUMENTS

| DE | 3724442 A1 | 7/1987 |
| DE | 3734442 C2 | 10/1987 |
| EP | 0389063 A2 | 3/1990 |
| EP | 0439182 A2 | 7/1991 |
| EP | 0439182 A3 | 7/1991 |
| EP | 0439182 B1 | 4/1996 |
| EP | 1201753 A1 | 5/2002 |
| WO | WO 90/01069 A1 | 2/1990 |
| WO | WO 91/12079 A1 | 8/1991 |
| WO | WO 92/02638 A1 | 2/1992 |
| WO | WO 92/08808 A1 | 5/1992 |
| WO | WO 95/01359 A1 | 1/1995 |
| WO | WO 96/41811 A1 | 12/1996 |
| WO | WO 97/05248 A2 | 2/1997 |
| WO | WO 97/05248 A3 | 2/1997 |
| WO | WO 98/04730 A1 | 2/1998 |
| WO | WO 99/16781 A2 | 4/1999 |
| WO | WO 99/16781 A3 | 4/1999 |
| WO | 0009746 A1 | 2/2000 |
| WO | WO 00/09746 A1 | 2/2000 |
| WO | WO 01/37291 A1 | 5/2001 |
| WO | WO 01/60517 A2 | 8/2001 |
| WO | 03057910 A2 | 7/2003 |
| WO | 03057910 A3 | 7/2003 |
| WO | WO 2005/064010 A1 | 7/2005 |

OTHER PUBLICATIONS

EP 6025539.5, PCT Search Report, Mar. 26, 2007.
Abramson, R., et al., 1993, "Nucleic Acid Amplification Technologies", *Current Opinion in Biotechnology*, 4:41-47.
Alderton, R., et al., 1992, "Magnetic Bead Purification of M13 DNA Sequencing Templates", *Analytical Biochemistry*, 201:166-169.
Barany, Francis, 1991, "The Ligase Chain Reaction in a PCR World", *PCR Methods and Applications*, 1:5-16.
Barany, Francis, 1991, "Genetic Disease Detection and DNA Amplification Using Cloned Thermostable Ligase", *Proc. Natl. Acad. Sci. USA*, 88:189-193.
Guatelli, J. C., et al., 1990, "Isothermal, In Vitro Amplification of Nucleic Acids by a Multienzyme Reaction Modeled After Retroviral Replication", *Proc. Natl. Acad. Sci. USA*, 87:1874-1878.
Jakobi , R., et al., 1988, "Filter-Supported Preparation of λ Phange DNA", *Analytical Biochemistry*, 175:196-201.
Kwoh, D.Y, et al., 1989, "Transcription-based Amplification System and Detection of Amplified Human Immunodeficiency Virus Type 1 with a Bead-Based Sandwich Hybridization Format", *Proc. Natl. Acad. Sci. USA*, 86:1173-1177.
Marko, M. A., et al., 1982, "A Procedure for the Large-Scale Isolation of Highly Purified Plasmid DNA Using Alkaline Extraction and Binding to Glass Powder", *Analytical Biochemistry*, 121:382-387.
Vogelstein, B., et al., 1979, "Preparative and Analytical Purification of DNA from Agarose", *Proc. Natl. Acad. Sci. USA*, 76-2:615-619.
Walsh, C., "Enzymatic Reaction Mechanisms", W. H. Freeman and Company, San Francisco, California, 1979.

(Continued)

Primary Examiner — Robert A Zeman
(74) Attorney, Agent, or Firm — Olga Kay

(57) ABSTRACT

This invention relates to a composition comprising a chaotropic agent, a buffering substance, and 0.5 to 5% (V/V) polidocanol or a derivative thereof. The invention is further related to uses of this composition and to a kit comprising the composition according to the invention. The invention is further related to a method for the detection of a nucleic acid in a biological sample comprising the steps of incubating the biological sample in the presence of a chaotropic agent, a buffering substance, and 0.5 to 5% (V/V) polidocanol or a derivative thereof, optionally isolating the nucleic acid, optionally amplifying the nucleic acid, and detecting the nucleic acid. The invention is further related to a method for the purification of a nucleic acid in a biological sample comprising the steps of incubating the biological sample in the presence of a chaotropic agent, a buffering substance, and 0.5 to 5% (V/V) polidocanol or a derivative thereof and isolating the nucleic acid thereby purifying the nucleic acid.

7 Claims, 4 Drawing Sheets

OTHER PUBLICATIONS

Whelen, A. C., et al., 1996, "The Role of Nucleic Acid Amplification and Detection in the Clinical Microbiology Laboratory", *Annu. Rev. Microbiol.*, 50:349-373.

Wu, D. Y., et al., 1989, "The Ligation Amplification Reaction (LAR)—Amplification of Specific DNA Sequences Using Sequential Rounds of Template-Dependent Ligation", *Genomics*, 4:560-569.

Ausubel, F., et al. (eds), "Current Protocols in Molecular Biology", John Wiley & Sons, Inc., New York, vol. 1-3:1998.

Lottspeich, F., et al. (eds), "Bioanalytik", Spektrum Akademischer Verlag, Berlin, Germany, 1998.

Sambrook, J., et al. (eds), "Molecular Cloning: A Laboratory Manual", Cold Springs Harbor Laboratory Press, Second Edition, 1989.

| used Lysis buffer | | + 1% DTT | | | | | | used Lysis buffer / formulation |
|---|---|---|---|---|---|---|---|---|
| | | Tgt CT | IQS CT | TgtInc AbsNorm | IQSInc AbsNorm | Δ CT | Hit Rate | |
| RL 8.1b | ave | 40,07 | 31,28 | 4,274 | 26,206 | -8,79 | 22/24 91.67% | 4M GuSCN 50mM Na-Citrat 1% DTT 15% Polidocanol |
| | sd | 2,22 | 0,14 | 2,675 | 1,635 | 2,25 | | |
| | cv% | 5,55 | 0,45 | 62,58 | 6,24 | -25,60 | | |
| Repetition | ave | 40,12 | 31,28 | 4,33 | 25,89 | -8,81 | 21/24 87.50% | |
| | sd | 1,94 | 0,19 | 2,63 | 1,85 | 1,93 | | |
| | cv% | 4,82 | 0,62 | 60,86 | 7,16 | -21,95 | | |
| RL 8.2b | ave | 40,05 | 30,93 | 5,389 | 28,125 | -9,12 | 23/24 95.83% | 4M GuSCN 50mM Na-Citrat 1% DTT 10% Polidocanol |
| | sd | 3,11 | 0,21 | 3,130 | 1,925 | 3,05 | | |
| | cv% | 7,77 | 0,69 | 58,09 | 6,85 | -33,43 | | |
| Repetition | ave | 40,26 | 31,04 | 3,98 | 26,83 | -9,23 | 22/24 91.67% | |
| | sd | 2,14 | 0,16 | 2,26 | 1,87 | 2,13 | | |
| | cv% | 5,31 | 0,52 | 56,78 | 6,96 | -23,10 | | |
| RL 8.3b | ave | 39,63 | 30,81 | 5,70 | 28,53 | -8,83 | 24/24 100.00% | 4M GuSCN 50mM Na-Citrat 1% DTT 5% Polidocanol |
| | sd | 1,87 | 0,26 | 2,96 | 1,28 | 1,84 | | |
| | cv% | 4,72 | 0,84 | 51,90 | 4,49 | -20,83 | | |
| RL 8.4b | ave | 39,28 | 30,30 | 5,901 | 28,899 | -8,98 | 23/24 95.83% | 4M GuSCN 50mM Na-Citrat 1% DTT 1% Polidocanol |
| | sd | 1,17 | 0,18 | 2,552 | 1,291 | 1,18 | | |
| | cv% | 2,97 | 0,58 | 43,25 | 4,47 | -13,15 | | |
| RL 8.5b | ave | 44,23 | 35,03 | 6,836 | 28,771 | -9,13 | 2/24 8.33% | 4M GuSCN 50mM Na-Citrat 1% DTT 0,1% Polidocanol |
| | sd | 3,31 | 0,22 | 6,316 | 1,786 | 3,35 | | |
| | cv% | 7,48 | 0,62 | 92,39 | 6,21 | -36,73 | | |

FIGURE 1

| used Lysis buffer | | - DTT | | | | | Hit Rate | used Lysis buffer / formuliation |
|---|---|---|---|---|---|---|---|---|
| | | Tgt CT | IQS CT | TgtInc AbsNorm | IQSInc AbsNorm | Δ CT | | |
| RL 8.1a | ave | 40,75 | 31,21 | 2,005 | 19,716 | -9,35 | 6/24 25% | 4M GuSCN 50mM Na-Citrat 0% DTT 15% Polidocanol |
| | sd | 2,06 | 0,23 | 0,822 | 1,871 | 2,09 | | |
| | cv% | 5,06 | 0,75 | 41,01 | 9,49 | -22,34 | | |
| RL 8.2a | ave | 44,51 | 31,11 | 1,182 | 19,759 | -13,49 | 7/24 29.17% | 4M GuSCN 50mM Na-Citrat 0% DTT 10% Polidocanol |
| | sd | 3,20 | 0,20 | 0,684 | 1,808 | 3,18 | | |
| | cv% | 7,18 | 0,63 | 57,86 | 9,15 | -23,55 | | |
| RL 8.3a | ave | 42,67 | 30,88 | 1,571 | 21,183 | -11,75 | 11/24 45.83% | 4M GuSCN 50mM Na-Citrat 0% DTT 5% Polidocanol |
| | sd | 3,69 | 0,25 | 0,892 | 1,777 | 3,73 | | |
| | cv% | 8,66 | 0,81 | 56,79 | 8,39 | -31,75 | | |
| RL 8.4a | ave | 43,23 | 30,76 | 1,547 | 21,816 | -12,48 | 15/24 62.50% | 4M GuSCN 50mM Na-Citrat 0% DTT 1% Polidocanol |
| | sd | 3,04 | 0,22 | 1,062 | 1,943 | 3,17 | | |
| | cv% | 7,04 | 0,71 | 68,68 | 8,91 | -25,37 | | |
| RL 8.5a | ave | N/A | 36,16 | N/A | 23,885 | N/A | 0/24 0% | 4M GuSCN 50mM Na-Citrat 0% DTT 0,1% Polidocanol |
| | sd | N/A | 0,28 | N/A | 1,990 | N/A | | |
| | cv% | N/A | 0,78 | N/A | 8,33 | N/A | | |

FIGURE 2

| used Lysis buffer | Hit Rate | Hits (x / 23) | Hits (x / 23) | used Lysis buffer / Formulation |
|---|---|---|---|---|
| RL 8.3a | 60.87% | 14 | 14 | 4M GuSCN<br>50mM Na-Citrat<br>0% DTT<br>5% Polidocanol |
| 0170NN | 86.97% | 20 | 20 | 4M GuSCN<br>50mM Na-Citrat<br>0% DTT<br>3% Polidocanol |
| RL 6.2 | 86.97% | 20 | 20 | 4M GuSCN<br>50mM Na-Citrat<br>0% DTT<br>1,5% Polidocanol |
| RL 8.1a | 69.57% | 16 | 16 | 4M GuSCN<br>50mM Na-Citrat<br>0% DTT<br>1% Polidocanol |
| RL 8.5a | 4.35% | 1 | 1 | 4M GuSCN<br>50mM Na-Citrat<br>0% DTT<br>0,1% Polidocanol |

FIGURE 3

NUCLEIC ACID ISOLATION USING POLIDOCANOL AND DERIVATIVES

CROSS-REFERENCES TO RELATED APPLICATIONS

The present application is a divisional of a co-pending application Ser. No. 12/001,670, filed on Dec. 11, 2007, which claims the benefit of EP Appl. No. 06025539.5 filed Dec. 11, 2006, the entire contents of both applications are hereby incorporated by reference in its entirety.

FIELD OF THE INVENTION

This invention relates to a composition comprising a chaotropic agent, a buffering substance, and 0.5 to 5% (V/V) polidocanol or a derivative thereof. The invention is further related to uses of this composition and to a kit comprising the composition. The invention is further related to a method for the detection of a nucleic acid in a biological sample comprising the steps of incubating the biological sample in the presence of a chaotropic agent, a buffering substance, and 0.5 to 5% (V/V) polidocanol or a derivative thereof, optionally isolating the nucleic acid, optionally amplifying the nucleic acid, and detecting the nucleic acid. The invention is further related to a method for the purification of a nucleic acid in a biological sample comprising the steps of incubating the biological sample in the presence of a chaotropic agent, a buffering substance, and 0.5 to 5% (V/V) polidocanol or a derivative thereof and isolating the nucleic acid, thereby purifying the nucleic acid.

BACKGROUND OF THE INVENTION

Many biological substances, especially nucleic acids, present special challenges in terms of isolating them from their natural environment. On the one hand, they are often present in very small concentrations and, on the other hand, they are often found in the presence of many other solid and dissolved substances e.g. after lysis of cells. This makes them difficult to isolate or to measure, in particular in biospecific assays which allow the detection of specific analytes, e.g. nucleic acids, or specific analyte properties and play a major role in the field of diagnostics and bioanalytics in research and development. Examples for biospecific assays are hybridisation assays, immuno assays and receptor-ligand assays.

Hybridisation assays use the specific base-pairing for the molecular detection of nucleic acid analytes e.g. RNA and DNA. Hence, oligonucleotide probes with a length of 18 to 20 nucleotides may enable the specific recognition of a selected complementary sequence e.g. in the human genome. Another assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of desoxynucleotide triphosphates in several cycles.

As described above, before the biological substances may be analysed in one of the above-mentioned assays or used for other processes, it has to be isolated or purified from biological samples containing complex mixtures of different components as e.g. proteinaceous and non-proteinaceous components. Often, for the first steps, processes are used which allow the enrichment of the component of interest, e.g. the nucleic acid. Frequently, these are contained in a bacterial cell, a fungal cell, a viral particle, or the cell of a more complex organism, such as a human blood cell or a plant cell. The component of interest can also be called a "target component".

To release the contents of said cells or particles, they may be treated with enzymes or with chemicals to dissolve, degrade or denature the cellular walls of such organisms. This process is commonly referred to as lysis. The resulting solution containing such lysed material is referred to as lysate. A problem often encountered during lysis is that other enzymes degrading the target component, e.g. desoxyribonucleases or ribonucleases degrading nucleic acids, come into contact with the component of interest during lysis. These degrading enzymes may also be present outside of the cells spatially separated in different cellular compartments before lysis and come into contact with the target component after lysis. Other components released during this process may be e.g. endotoxins belonging to the family of lipopolysaccharides which are toxic to cells and can cause problems for products intended to be used in human or animal therapy.

There are a variety of means to tackle this problem mentioned-above. It is common to use chaotropic agents as e.g. guanidinium thiocyanate or anionic, cationic, zwitterionic or non-ionic detergents when nucleic acids are intended to be set free. It is also an advantage to use proteases which rapidly degrade these enzymes or unwanted proteins. However, this may produce another problem as the said substances or enzymes can interfere with reagents or components in subsequent steps.

Enzymes which can be advantageously used in such lysis or sample preparation processes mentioned-above are enzymes which cleave the amide linkages in protein substrates and which are classified as proteases, or (interchangeably) peptidases (See Walsh, C., Enzymatic Reaction Mechanisms (1979) chapter 3, W. H. Freeman and Company, San Francisco). Proteases which have been used are e.g. alkaline proteases (WO 98/04730) or acid proteases (U.S. Pat. No. 5,386,024). The protease which is widely used for sample preparation for the isolation of nucleic acids is proteinase K from Tritirachium album (see e.g. Sambrook, J., et al.: Molecular Cloning (1989) Cold Spring Harbor University Press, NY, USA) which is active around neutral pH and belongs to a family of proteases known to the person skilled in the art as subtilisins. A subtilisin is a serine protease produced by Gram-positive bacteria or fungi.

In the next steps of the sample preparation which follow on the lysis step, the target component is further enriched. If the target component is a nucleic acid, the target nucleic acid is normally extracted from the complex lysis mixtures before it is used in a probe-based assay.

There are several methods for the extraction of nucleic acids:
  sequence-dependent or biospecific methods, e.g.:
  affinity chromatography
  hybridisation to immobilised probes
  sequence-independent or physico-chemical methods, e.g.:
  liquid-liquid extraction with e.g. phenol-chloroform
  precipitation with e.g. pure ethanol
  extraction with filter paper
  extraction with micelle-forming agents as cetyl-trimethyl-ammonium-bromide
  binding to immobilised, intercalating dyes, e.g. acridine derivatives
  adsorption to silica gel or diatomic earths
  adsorption to magnetic glass particles (MGP) or organo silane particles under chaotropic conditions.

SUMMARY OF THE INVENTION

Therefore, it was an object of the present invention to provide a new composition for the lysis of a biological sample and/or for influencing or enhancing the binding behaviour of nucleic acids to silica surfaces.

In one embodiment, there is provided a composition comprising a chaotropic agent, a buffering substance, and 0.5 to 5% (V/V) polidocanol or a derivative thereof.

In another embodiment, the composition according to the invention is used for the purification of a nucleic acid, for binding a nucleic acid to a solid surface or for the detection of a nucleic acid.

In yet another embodiment, a method for the detection of a nucleic acid in a biological sample is provided comprising:
a) incubating the biological sample in the presence of a chaotropic agent, a buffering substance, and 0.5 to 5% (V/V) polidocanol or a derivative thereof,
b) optionally isolating the nucleic acid,
c) optionally amplifying the nucleic acid, and
d) detecting the nucleic acid.

In still another embodiment, a method for the purification of a nucleic acid in a biological sample is provided comprising:
a) incubating the biological sample in the presence of a chaotropic agent, a buffering substance, and 0.5 to 5% (V/V) polidocanol or a derivative thereof,
b) isolating the nucleic acid thereby purifying the nucleic acid.

The term "polidocanol" or "polydocanol" relates to a chemical compound or composition consisting of a mixture of polyethylene glycol monododecyl ethers averaging about 9 ethylene oxide groups per molecule. It could be described by the molecular formula $(C_2H_4O)_nC_{12}H_{26}O$ or $HO(CH_2CH_2O)_n(CH_2)_{11}CH_3$ whereby n is about or exactly 9, i.e. the median number of ethylene glycol moieties is about or exactly 9 as a result of the production method wherein lauryl alcohol is reacted with ethylene oxide (ethoxylation). This means that the molecular weight is about 600 g/mol. Other names for this compound are 3,6,9,12,15,18,21,24,27-nonaoxanonatriacontan-1-ol, dodecyl nonaethylene glycol ether, dodecylnonaglycol, polyoxyethylene 9 lauryl ether or laureth 9. The compound is also a suitable emulsifying and solubilizing agent for oil/water (O/W) types of cosmetic and dermatological emulsions, a topical anaesthetics, a spermicide and surfactant or a sclerosing agent in treatment of varicose veins. The compound can be obtained e.g. from Kolb, Hedingen, Switzerland (Sympatens-AL/090 P). According to the invention, the term "polidocanol" or "polydocanol" shall however also refer to the chemically defined and purified compounds with the formula $(C_2H_4O)_9C_{12}H_{26}O$ or $HO(CH_2CH_2O)_9(CH_2)_{11}CH_3$. "Polidocanol" is a white ointment-like substance at room temperature and becomes a clear, colorless to slightly yellow liquid at approximately 30° C. Therefore, for preparing polidocanol-containing compositions polidocanol can be pipetted when heated e.g. in a water bath to e.g. 37° C. or 40° C. or added as a solid substance at room temperature. Therefore, according to the invention 2.37 l (liquid) polidocanol (at little more than 30° C., preferably 37° C.), equal 2.365 kg solid polidocanol (at little less than 30° C., preferably room temperature, i.e. between 20 to 25° C.). The resulting compositions or solutions denote the polidocanol content as % (V/V) or % (W/V). The term "(V/V)" shall mean volume per volume and "(W/V)" shall mean weight per volume. The preferred solvent or major component of the composition shall be water, i.e. preferably these are aqueous compositions or aqueous solutions.

The term "derivative of polidocanol" or "derivative of polydocanol" relates to "polidocanol" or "polydocanol" that is chemically derivatized but has properties, in particular properties in the methods according to the invention, that are identical or very similar to the properties of "polidocanol" or "polydocanol".

Another word for "composition" is solution in the context of the invention.

"Biological samples" are samples which are taken from a plant or an animal (including a human being) and are solid or liquid. Specific examples are described in more detail below.

BRIEF DESCRIPTION OF THE FIGURES

FIG. 1 shows the results of analyses of WHO International HBV Standards prepared using the lysis buffer of several different embodiment of the invention.

FIG. 2 shows the results of analyses of WHO International HBV Standards prepared using the lysis buffer of several different embodiment of the invention.

FIG. 3 shows the results of analyses of WHO International HBV Standards prepared using the lysis buffer of several different embodiment of the invention.

DETAILED DESCRIPTION OF THE INVENTION

Figure 4:
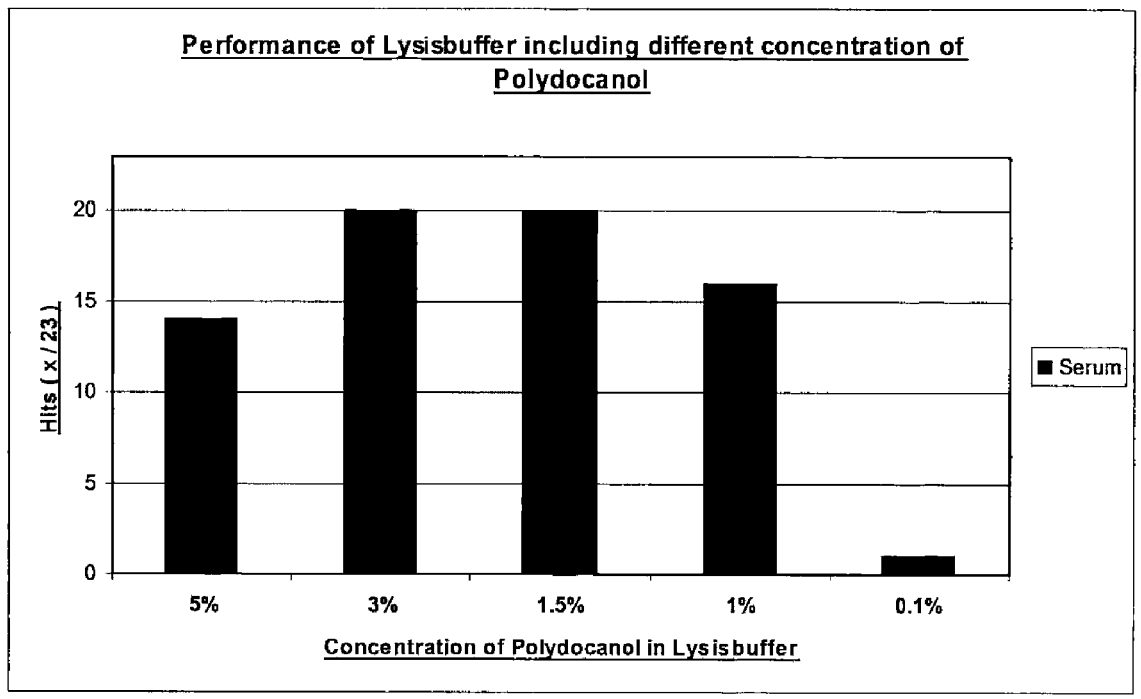
FIG. 4 is a bar graph showing the performance of several different lysis buffers according to the present invention.

In an embodiment of the invention, a composition is provided comprising
a chaotropic agent,
a buffering substance, and
0.5 to 5% (V/V) polidocanol or a derivative thereof.

In one embodiment of the invention, the composition comprises 0.5 to 4.9% (V/V) polidocanol, or a derivative thereof, or 0.5 to 4.5% (V/V) polidocanol or a derivative thereof, or 0.5 to 3% (V/V) polidocanol, or a derivative thereof: or the composition comprises 0.75 to 1.75% (V/V) polidocanol or a derivative thereof.

In another embodiment of the invention, the composition comprises 1 to 4.5% (V/V) polidocanol or a derivative thereof, or the composition comprises 1.5 to 3% (V/V) polidocanol or a derivative thereof.

In another embodiment of the invention, the chaotropic agent is guanidinium thiocyanate, guanidinium isothiocyanate, guanidinium chloride or urea. However, potassium chlorate ($KClO_4$) or potassium iodide (KI) are also possible.

In another embodiment of the invention, the buffering substance comprises Tris-(hydroxymethyl)-aminomethane (TRIS), phosphate, N-(2-hydroxyethyl)-piperazine-N'-(2-ethanesulfonic acid) (HEPES), acetate or citrate.

In another embodiment of the invention, the pH of the composition is acidic more particularly, the pH of the composition may be between 3 and 5.

In still another embodiment of the invention, the composition may further comprise a reducing agent, such as dithiothreitol (DTT).

In one embodiment of the invention, the composition comprises 4 M guanidinium thiocyanate, 50 mM Na-Citrate, 1% (V/V) DTT, 3% (V/V) polidocanol, pH 4.

In still another embodiment of the invention, the composition may further comprise a protease.

In a another embodiment of the invention, the composition is used in a process for the purification of a nucleic acid, for binding a nucleic acid to a solid surface or for the detection of a nucleic acid.

The invention further contemplates a kit of parts characterized in that it contains the composition according to the invention or components for creating the composition according to the invention. Such kits known in the art may further comprise plastics ware which can be used during the sample preparation procedure as e.g. microtitre plates in the 96 or 384 well format or reaction tubes manufactured e.g. by Eppendorf, (Hamburg, Germany) and all other reagents for carrying out the method according to the invention. Therefore, the kit can additionally contain a nucleic acid binding material. In some embodiments, the nucleic acid binding material comprises a material with a silica surface. The material with a silica surface may be a glass. In some embodiments, the nucleic acid binding material may comprise magnetic glass particles. These components of the kit according to the invention may be provided separately in tubes or storage containers. Depending on the nature of the components, these may be provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which may be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

The kit according to the invention may be used for the purification of nucleic acids in research, bioanalytics or diagnostics. The kit according to the invention or the method according to the invention using such a kit may be adaptable for use in a high-throughput format, i.e. in an automatized method which allows the analysis of a high number of different samples. For example, the components of the kit may be arranged for easy use in a particular high throughput instrument; may be at concentrations suitable for use in such an instrument; may contain other components adapted for use in such an instrument; or may be be adapted for use in a particular high throughput method.

In an embodiment of the invention, a method for the detection of a nucleic acid in a biological sample is provided comprising:
 a) incubating the biological sample in the presence of a chaotropic agent, a buffering substance, and 0.5 to 5% (V/V) polidocanol or a derivative thereof,
 b) optionally isolating the nucleic acid,
 c) optionally amplifying the nucleic acid, and
 d) detecting the nucleic acid.

In step a) of the method above, the biological sample amyis lysed releasing the biological substances including nucleic acids contained in the biological sample. Alternately, a lysis step may be preferred prior to inculation of the sample in the cited compositions. With regard to the general parameters for a lysis procedure to obtain nucleic acids, special reference is made to Sambrook, J., et al.: Molecular Cloning, A Laboratory Manual, $2^{nd}$ edition (1989) Cold Spring Harbour Laboratory Press, NY, USA, and Ausubel, F., et al.: Current Protocols in Molecular Biology (1987) John Wiley & Sons, Inc., NY, USA. A combination of procedures for lysis using the composition according to the invention is applicable as well. For instance, lysis can be performed using ultrasound, high pressure, or by shear forces. It is also often the case, that proteases that degrade the proteins present in the biological sample are added. The protease may be added in solid form e.g. as a tablet or a powder or in a dissolved form in a buffered or unbuffered solution. Examples of proteases are proteinase K or another protease from *Bacillus subtilis* described in EP 1 201 753.

The nucleic acid may be amplified with the polymerase chain reaction (PCR) which specifically amplifies target sequences to detectable amounts. Therefore, in one embodiment of the invention, in the amplifying step c) the nucleic acid is amplified by the polymerase chain reaction. Other possible amplification reactions are the Ligase Chain Reaction (LCR, Wu, D. Y., and Wallace, R. B., Genomics 4 (1989) 560-569 and Barany, F., Proc. Natl. Acad. Sci. USA 88 (1991) 189-193); Polymerase Ligase Chain Reaction (Barany, F., PCR Methods and Appl. 1 (1991) 5-16); Gap-LCR (PCT Patent Publication No. WO 90/01069); Repair Chain Reaction (EP 0 439 182), 3SR (Kwoh, D. Y., et al., Proc. Natl. Acad. Sci. USA 86 (1989) 1173-1177; Guatelli, C. J., et al., Proc. Natl. Acad. Sci. USA 87 (1990) 1874-1878; PCT Patent Publication No. WO 92/08808), and NASBA (U.S. Pat. No. 5,130,238). Further, there are strand displacement amplification (SDA), transcription mediated amplification (TMA), and Qβamplification (for a review see e.g. Whelen, A. C., and Persing, D. H., Annu. Rev. Microbiol. 50 (1996) 349-373; Abramson, R. D., and Myers, T. W., Current Opinion in Biotechnology 4 (1993) 41-47).

A suitable detection method is the realtime PCR method disclosed in WO 92/02638 and the corresponding U.S. Pat. No. 5,210,015, U.S. Pat. No. 5,804,375, U.S. Pat. No. 5,487,972. In detail, the target nucleic acid component is detected by a process comprising contacting the sample with an oligonucleotide containing a sequence complementary to a region of the target nucleic acid component and a labeled oligonucleotide containing a sequence complementary to a second region of the same target nucleic acid component sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is near to or adjacent to the 5'-end of the labeled oligonucleotide. Then this mixture is treated with a template-dependent nucleic acid polymerase. In one embodiment, the nuclease has a 5' to 3' nuclease activity and the mixture is treated under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. The method performed in the TaqMan® instrument eliminates the need for a solid phase bound reaction complex to be formed and made detectable. In more general terms, a procedure for the purification of a (at least one) target nucleic acid component followed by a detection step is disclosed wherein the amplification and/or detection reaction is a homogeneous solution-phase.

The nucleic acid may be determined or detected by standard analytical methods known to the person skilled in the art and described e.g. in Sambrook, J., et al.: Molecular Cloning (1989) Cold Spring Harbor University Press, NY, USA or in Lottspeich, F., and Zorbas, H. (eds.), Bioanalytik, $1^{st}$ edition (1998) Spektrum Akademischer Verlag GmbH, Heidelberg, Berlin, Germany. Preferably, the amount of the nucleic acid is determined with the methods described therein. There may be also further purification steps before the DNA detection step is carried out as e.g. a precipitation step. The detection methods may include but are not limited to the binding or intercalating of specific dyes as ethidium bromide or SYBR Green, which intercalates into the double-stranded-DNA and changes its fluorescence. The purified DNA may also be separated by electrophoretic methods optionally after a restriction digest and visualized thereafter. There are also probe-based assays which exploit the oligonucleotide hybridisation to specific sequences and subsequent detection of the hybrid, such as molecular beacons, Scorpions, FRET probes and hybridization probes. It is also possible to sequence the DNA after further steps known to the expert in the field. Other methods apply a diversity of DNA sequences to a silicon chip to which specific probes are bound and yield a signal when a complementary sequences bind.

In an embodiment of the invention, a method for the purification of a nucleic acid in a biological sample is provided comprising:
 a. incubating the biological sample in the presence of a chaotropic agent, a buffering substance, and 0.5 to 5% (V/V) polidocanol or a derivative thereof, and
 b. isolating the nucleic acid, thereby purifying the nucleic acid.

The incubation conditions of step a) of both methods according to the invention are preferably prepared by adding a composition according to the invention to the biological sample. In one embodiment of the invention, in step a) the biological sample is incubated in the presence of a chaotropic agent, a buffering substance, and 0.5 to 4.9% (V/V) polidocanol or a derivative thereof, 0.5 to 4.5% (V/V) polidocanol or a derivative thereof, 0.5 to 3% (V/V) polidocanol or a derivative thereof, preferably 0.75 to 1.75% (V/V) polidocanol or a derivative thereof. Preferably, the isolating step b) of the method comprises binding the nucleic acid to a material with an affinity to nucleic acids, preferably a material with a silica surface, optionally washing the nucleic acid bound to the material and eluting the nucleic acid from the material. Preferably, the material with a silica surface is a composition comprising magnetic glass particles. In the most preferred embodiment, the washing step is not optional.

In order to bind the nucleic acid to a material with an affinity thereto, the lysis mixture is brought in contact with the material with an affinity to the nucleic acid under conditions in which the nucleic acid binds to the surface of the material. The conditions for this are basically known to the expert in the field. They also depend on the method by which the nucleic acid is bound to the surface. For example, if modified nucleic acids are the nucleic acids, the binding can take place via the groups of nucleic acids that represent the modification, e.g., biotin via binding with streptavidin-coated surfaces.

If unmodified nucleic acids are to be isolated, a direct binding of the nucleic acids to a material with a silica surface is preferred because among other reasons the nucleic acids do not have to be modified and even native nucleic acids can be bound. These processes are described in detail by various documents. In Vogelstein, B., and Gillespie, D., Proc. Natl. Acad. USA 76 (1979) 615-619, for instance, a procedure for binding nucleic acids from agarose gels in the presence of sodium iodide to ground flint glass is proposed. The purification of plasmid DNA from bacteria on glass dust in the presence of sodium perchlorate is described in Marko, M. A., et al., Anal. Biochem. 121 (1982) 382-387. In DE 3734442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi, R., et al., Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. The use of magnetic particles to immobilize nucleic acids after precipitation by adding salt and ethanol is more advantageous and described e.g. in Alderton, R. P., et al., Anal. Biochem. 201 (1992) 166-169 and WO 91/12079. In this procedure, the nucleic acids are agglutinated along with the magnetic particles. The agglutinate is separated from the original solvent by applying a magnetic field and performing a wash step. After one wash step, the nucleic acids are dissolved in a Tris buffer. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. The most preferred MGPs are those described in WO 01/37291.

In detail, the procedure for binding the nucleic acid to glass particles can be described as follows. It is preferably performed in the presence of chaotropic agents or salts with a concentration of between 1 and 8 mol/l, and preferably between 2 and 6 mol/l. Chaotropic salts can be e.g. sodium iodide, sodium perchlorate, guanidinium thiocyanate, guanidinium isothiocyanate or guanidinium hydrochloride. Other substances are also possible. The purification effect results from the behavior of DNA or RNA to bind to material with a glass surface under these conditions i.e. in the presence of certain concentration of a chaotropic agent, higher concentrations of organic solvents or under acidic conditions. To bring the sample in contact with the material with an affinity to the nucleic acid, the sample is mixed with the material and incubated for a period of time sufficient for the binding to occur. Experts are usually familiar with the duration of the incubation step from procedures for performing treatment with non-magnetic particles. This step can be optimized by determining the quantity of immobilized biological material on the surface at different points in time. Incubation times of between 10 seconds and 30 minutes can be appropriate for nucleic acids. After incubation, the bound nucleic acid is separated from the liquid. This may be achieved in general by gravity or in the convenient case of nucleic acids bound to magnetic glass particles by separating the material bound to the magnetic particles by applying a magnetic field. For instance, the magnetic particles can be pulled to the wall of the vessel in which incubation was performed. The liquid containing the sample contents that were not bound to the magnetic particles can then be removed. The removal procedure used depends on the type of vessel in which incubation was performed. Suitable steps include removing the liquid via pipetting or aspiration. The material with the bound DNA or RNA may then be washed at least once e.g. with a mixture of 70 volume parts ethanol with 30 volume parts water ("70% Ethanol") or by suitable wash solutions not containing alcohol. A wash solution is used that does not cause the nucleic acid to be released from the material surface but that washes away the undesired contaminants as thoroughly as possible. This wash step preferably takes place by incubating the material with the bound nucleic acid with the wash solution. The material is preferably resuspended during this step. The contaminated wash solution is preferably removed just as in the step described above for binding the biological material. After the last wash step, the material can be dried briefly in a vacuum, or the fluid can be allowed to evaporate. A pretreatment step using acetone may also be performed. Afterwards, the conditions may be reversed, e.g. the concentration of the chaotropic agent or organic solvent is decreased to elute the DNA or RNA bound to the material. Preferably, the process of separating the magnetic glass particles from the rest of the sample is done by pelleting the immobilized nucleic acid, e.g. by gravity force or by the use of a magnet in the case of magnetic glass particles and removal of the supernatant. Then the magnetic glass particles with the immobilized biological material are resuspended in a solution with no or only a low amount of chaotropic agent and/or organic solvent. Alternatively, the suspension can be diluted with a solution with no or only a low amount of chaotropic agent and/or organic solvent. Buffers of this nature are known from DE 3724442 and Jakobi, R., et al., Anal. Biochem. 175 (1988) 196-201. The elution buffers with a low salt content are in particular buffers with a content of less than 0.2 mol/l. In an especially preferred embodiment, the elution buffer contains the substance Tris for buffering purposes. In another special embodiment, the elution buffer is demineralized water. The solution containing purified DNA or RNA can now be used for other reactions.

For washing and binding steps, preferably liquids are used which are suitable for processes in molecular biology, in particular desoxyribonucleic acid (DNA) or ribonucleic acid (RNA) purification processes which make use of the binding of these substances to glass particles under certain conditions. Preferred liquids comprise alcohols and/or ketones or any mixtures thereof with water. Alcohols shall include according to the invention preferably primary, secondary or tertiary alcohols of the general formula R-OH where the R stands for the general formula —($-CH_2$)$_n$—$CH_3$ with n>=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water. In another embodiment of the invention the liquid comprises ketones as e.g. acetone.

The material with an affinity to nucleic acids and the target nucleic acid component comprises a material with a silica surface/The material with a silica surface may be a glass, e.g., a composition comprising magnetic glass particles. The steps are performed essentially as already describe above. In summary, magnetic glass particles are added to the lysis mixture comprising the nucleic acid. After a suitable period of time for adsorption to take place—which can be optimized by mechanical agitation—the particles are separated from the surrounding fluid that contains additional components that are not to be detected. This is performed e.g., by applying a magnetic field via a magnet placed against the vessel wall and removing the remaining liquid from the tube. To remove further contaminants that may still be present, a wash step may be performed with a fluid that does not cause the nucleic acid to be released from the glass surface. An elution buffer having reagent conditions under which the nucleic acid is not bound to the glass surface and is eluted is added to remove the nucleic acid from the glass surface. These conditions are low salt conditions in particular. Depending on the intended further use of the nucleic acid, the fluid can now be separated from the particles and processed further. This separation step may be performed via application of a magnetic field so that the particles are separated from the eluate. An example of magnetic glass particles for this method are described in WO 01/37291, which is hereby incorporated by reference in its entirety.

The magnetic glass particles used in the present invention may be provided in different formulations. It is possible to provide them in the form of a tablet, as a powder or preferably as a suspension. In one embodiment of the invention these suspensions contain between 5 to 60 mg/ml magnetic glass particles (MGPs). In another embodiment the silica-containing material is suspended in an aqueous buffered solution which may optionally contain a chaotropic agent in a concentration of between 2 and 8 mol/l, or between 4 and 6 mol/l. Chaotropic salts are sodium iodide, sodium perchlorate, guanidinium thiocyanate, guanidinium isothiocyanate or guanidinium hydrochloride. Other compounds known to the expert in the field are also possible. A chaotropic agent according to the present invention is any chemical substance which disturbs the ordered structure of liquid water and has the effect that DNA or RNA binds to the magnetic glass particles if this agent is present in the DNA or RNA containing solution. Buffer systems which suitable for molecular biology purposes may be found e.g. in Sambrook et al. (1989), Molecular Cloning, Cold Spring Harbor University Press, New York, N.Y., USA. Preferred buffer substances are Tris-(hydroxymethyl)-aminomethane (TRIS), phosphate, N-(2-Hydroxyethyl)piperazine-N'-(2-ethanesulfonic acid) (HEPES), salts thereof or other suitable substances. Additionally, substances may be present which modify the ionic strength of the solution as e.g. NaCl, KCl or $CaCl_2$ or which are metal cation complexing agents as e.g. ethylene-diamine-tetra-acetic acid (EDTA) or the salts thereof. Other biological substances known to the expert in the field may also be present. The method according to the present invention is suitable for the purification of nucleic acids, i.e. RNA or DNA, from complex mixtures with other biological substances containing them. Thereby also mixtures of different nucleic acids may be purified, even mixtures containing a nucleic acid of interest in low abundance. In one embodiment of the invention mixtures of specific nucleic acids are purified, in which the nucleic acid(s) may be a minor component in terms of concentration (or may be present in low abundance).

After the steps described above, the nucleic acid isolated using the method according to the invention can now be used further as necessary. For instance, it can be used as a substrate for various enzymatic reactions. When nucleic acids are involved, they can be used for sequencing, radioactive or non-radioactive labelling, amplification of one or more of the sequences they contain, transcription, hybridization with labelled probe nucleic acids, translation or ligation.

In an embodiment of the invention, the biological sample is intended to comprise viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In one preferred embodiment of the invention the biological sample is a fluid from the human or animal body, such as blood, blood plasma, blood serum or urine. The blood plasma may contain EDTA, heparin or citrate. In an embodiment of the invention the biological sample comprises bacterial cells, eukaryotic cells, viruses or mixtures thereof. The biological sample can also be of a type used for environmental analysis, food analysis or molecular biology research, e.g. from bacterial cultures, phage lysates.

In another embodiment of the invention, the nucleic acid comprises DNA or RNA or both. The DNA or RNA or both may be derived from a microorganism or a virus. The virus can be hepatitis A virus (HAV), hepatitis B virus (HBV), hepatitis C virus (HCV), the human immunodeficiency virus (HIV), the human papilloma virus (HPV), cytomegalovirus (CMV) or parvovirus B19.

The method according to the invention may be used in research, bioanalytics in particular in diagnostics or in diagnostic investigations in medicine, i.e. in methods that are used to determine the cause of an illness or disorder in humans or in animals. Preferably the method according to the invention is used for diagnostic analysis or bioanalytics.

A one embodiment of the present invention uses the method or the kit of the present invention in automatable methods as e.g. described in WO 99/16781. Automatable method means that the steps of the method are suitable to be carried out with an apparatus or machine capable of operating with little or no external control or influence by a human being. Automatized method means that the steps of the automatable method are carried out with an apparatus or machine capable of operating with little or no external control or influence by a human being. In the same embodiments, only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. Preferred automatized methods are those which are carried out in a high-throughput format which means that the methods and the used machine or apparatus are optimized for a high-throughput of samples in a short time. In one embodiment of the invention the methods or the kits according to the present invention are used in semi-automatized process which means that some reaction steps may have to be done manually. In a preferred embodiment of the invention, a suspension containing MGPs according to the present invention is taken from a storage container and partial volumes are added to different reaction vessels. Reaction vessels may be reaction tubes made from plastics eventually in mictrotitreplate format contain 96 or 384 or more wells where a reaction can be carried out. However, these vessels may be made from other material e.g. from glass composite materials or steel. The vessels may be in any format useful in the automatized method chosen.

EXAMPLES

The following examples and figures are provided to aid the understanding of the present invention, the true scope of which is set forth in the appended claims. It is understood that modifications can be made in the procedures set forth without departing from the spirit of the invention.

Example 1

An improved method to perform rapid polymerase chain reactions is disclosed is used in the TaqMan® instrument (Roche, Mannheim, Germany) (see WO 92/02638). In this method, a probe with two labels is added to the amplification reaction. The two labels are in close proximity so that the two labels can undergo a fluorescence energy transfer (FRET) reaction and the fluorescence of the labels is quenched. This probe can hybridize to the amplificate and will be displaced and/or hydrolyzed by the thermostable DNA polymerase in an amplificate dependent manner. Thereby, the labels are released and the fluorescence is not further quenched whereby measurable fluorescence is obtained. The amount of the amplificate thereby correlates with the intensity of the emitted light of a certain wavelength. This specific PCR method can therefore be used to analyze how much nucleic acid was present in the tube and how effectively it can be amplified. The expert skilled in the art knows that other methods can be used for this evaluation as well.

Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i = N_o \times (1+E)^i$, where $N_o$=the number of target molecules at the start of the reaction, $N_i$=the number of target molecules at the completion of the i-th cycle, E=the efficiency of the amplification ($0 = \leq E = \leq 1$). During this geometric growth phase of the amplification, the number of cycles required to reach a particular threshold value ($C_T$ or $C_P$ value or crossing point) is inversely proportional to the logarithm of (1+E). Thus, the $C_T$ or $C_P$ value represents a measure of the reaction efficiency that allows comparisons between reactions. A decrease in the $C_T$ or $C_P$ value, which means that the reaction reached the threshold value in fewer cycles, indicates an increase in reaction efficiency. As the increase in amplification product is monitored by measuring the increase in reaction fluorescence, the $C_T$ or $C_P$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ or $C_P$ value or crossing point, was calculated by interpolating fluorescence measurements between cycles.

Example 1.1

Instruments and Materials Used for Both Experiments

Two data sets demonstrate an increase in sensitivity of molecular biological detection by using polidocanol concentrations from 1%-5% in the lysis and binding mixture.
Instruments:
COBAS® AmpliPrep/COBAS® TagMan® System with Docking Station (Roche Diagnostics GmbH, Mannheim, Germany)
device specific disposables (SPU, S-Tubes, K-Tubes, K-Tips)

Eppendorf pipettes and tips for the production of the sample material

Sample Material:
WHO 1$^{st}$ international Standard/HBV for HBV DNA NAT assays (National Biological Standards Board (NIBSC), South Mimms, Potters Bar, Hertfordshire, UK/NIBSC code: 97/746; conc.: 5E+05 International Units lyophilised/vial, reconstituted in 0.5 mL nuclease-free water, conc.: 1E+06 IU/mL)

human pool serum, PCR-negative tested for HBV

The HBV WHO Standard was diluted in serum to 12 IU/mL (experiment of data set 1) and to 10 IU/mL (experiment of data set 2) and frozen at −20° C. until preparation.

Reagent: COBAS AmpliPrep/COBAS TaqMan HBV Test, IVD:
Cassette 1: Beads
Cassette 3: Protease and Elution buffer
Cassette 4: Mastermix, spiked with additional 19 units ZO5 DNA polymerase
Manganese solution
Quantitation Standard The cassette 2 includes the Lysis buffers with the different polidocanol concentrations to be tested. The preparation thereof is described below.

The pH-value of all buffers is pH 4.

Composition of Lysis Buffer:
In the following, the preparation of exemplary buffers representing the preparation of all buffers is described:

Guanidinium thiocyanate (GuSCN) (94.53 g) was dissolved in PCR grade water (50 ml/0.25-0.5 of total buffer volume) at about 50° C. while stirring by a magnetic stir bar sodium citrate (2.94 g) was added and stirred for dissolving.

Polydocanol (30 ml, 20 ml, 10 ml, 2 ml, or 0.2 ml), fluidized in a water bath at 40° C., was added to the corresponding preparation (8.1a/b-8.5a/b) and cooled down to room temperature while stirring.

Dithiothreitol (DTT) (2 g) was added to the respective preparation (8.1b-8.5b)

pH was adjusted to pH 4.0 with HCl

Each preparation was filled up to 200 ml with PCR grade water, stirred again until each solution was homogenized and aliquoted to 80 ml into the lysis buffer bottles.

| Ingredients | Final concentration | |
| --- | --- | --- |
| Guanidiniumthiocyanat (GuSCN) | 4 M | These are the constant ingredients for the production of all Lysis buffer. |
| Tri-sodium-citrate-dihydrate | 50 mM | |
| PCR grade water | ./. | |
| Hydrochloric acid (HCl) | Used for setting to pH 4 | |
| 1,4-Dithiothreitol (DTT) | 0%/1% | These two ingredients were varied in their concentrations. |
| Polidocanol | 0.1%/1%/1.5%/3%/5%/15% (V/v) | |

The produced lysis buffers were also stored at 2° C.-8° C. as the remaining reagents and were manually filled into Cassette 2 of the system used.

Example 1.2

Method/Execution

The frozen sample material was thawed at 30° C. in a water bath. Subsequently, the automatic sample preparation in the COBAS® AmpliPrep instrument and the amplification and detection in the COBAS® TaqMan® instrument was performed according to the description of the manufacturer. The summation and the explanation of the test and the test principle is described in detail in the COBAS® AmpliPrep/COBAS® TaqMan® HBV Test Package Insert (Roche Diagnostics GmbH, Mannheim, Germany).

The hit rate determinations (FIGS. 1 and 2) were performed by analyzing 24 replicates at each polidocanol concentration and the number of negative results per number of replicates were determined. In addition target Ct-values, IQS Ct-values as well as target and IQS fluorescence values were measured and the difference between IQS and target Ct-values were calculated. Those Ct and fluorescence measurements were only performed and documented in FIGS. 1 and 2 for the sake of completeness. The decisive values are the hit rates which means the ratios of the negative and positive results. The Ct values say in this context only whether the sample is positive or negative.

Example 1.3

Data Analysis with Detailed Declaration of Used Lysis Buffers

Example 1.3.1

Data Set 1,

The used lysis buffers in the experiment for data set 1 were produced as described above. The following buffers were prepared:

| Identification | Polidocanol concentration (V/v) | DTT-concentration (V/v) |
| --- | --- | --- |
| RL 8.1a | 15% | 0% |
| RL 8.2a | 10% | 0% |
| RL 8.3a | 5% | 0% |
| RL 8.4a | 1% | 0% |
| RL 8.5a | 0.1% | 0% |
| RL 8.1b | 15% | 1% |
| RL 8.1b | 10% | 1% |
| RL 8.1b | 5% | 1% |
| RL 8.1b | 1% | 1% |
| RL 8.1b | 0.1% | 1% |

The results of lysis buffer RL 8.3a and TL 8.4a (FIG. 2) shows a tendency to an optimum, which depends on different polidocanol concentrations. Due to this results further experiments were performed, which analyzed more precisely the range between 0.1% and 5%.

Example 1.3.2

Data Set 2

The used Lysis buffers in the experiment for data set 2 are for the most part the same, which were used for data set 1. Inexistent buffers were used out of other productions or fresh produced:

| code | Polidocanol conc. (v/v) | DTT-conc. (v/v) |
|---|---|---|
| RL 8.3a | 5% | 0% |
| RL 6.2 | 1.5% | 0% |
| RL 8.1a | 1% | 0% |
| RL 8.5a | 0.1% | 0% |

(These buffer were already existing)

| | | |
|---|---|---|
| RL 8.1a | 15% | 0% |
| RL 6.3 | 0% | 0% |

(These buffers were used to produce the buffer including 3% polidocanol)

The results of the data set 2 confirm the polidocanol dependent optimum, which is at 1.5% to 3% polidocanol. (see FIG. 3 and FIG. 4)

Example 1.4

Summary

The polidocanol concentration has influence to the sensitivity of molecular biological detections as e.g. the methods performed in the COBAS® AmpliPrep/COBAS® TaqMan® System. The preferred range is between 1.5% and 3% polidocanol. Preferable is the formulation: 4M GuSCN, 50 mM Na-Citrate, 1% DTT, 3% (V/V) Polidocanol, pH 4.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for the purification of a nucleic acid in a biological sample, comprising:
    a) incubating the biological sample in the presence of a chaotropic agent, a buffering substance, a protease and 0.5 to 5% (V/V) polidocanol or a derivative thereof,
    b) isolating the nucleic acid, thereby purifying the nucleic acid.

2. The method according to claim 1, whereby the isolating step b) comprises binding the nucleic acid to a nucleic acid binding material, optionally washing the nucleic acid bound to the material and eluting the nucleic acid from the material.

3. The method according to claim 2, wherein the nucleic acid binging material comprises magnetic glass particles.

4. The method according to claim 1, wherein the biological sample is a fluid from the human or animal body, said fluid being selected from the group consisting of blood, blood plasma, blood serum and urine.

5. The method according to claim 1, wherein the nucleic acid comprises DNA or RNA or both.

6. The method according to claim 1, wherein the nucleic acid is derived from a microorganism or a virus.

7. The method according to claim 1, wherein the nucleic acid is derived from a member of the group consisting of a hepatitis A virus, hepatitis B virus, the hepatitis C virus, the human immunodeficiency virus or the cytomegalovirus.

* * * * *